(12) United States Patent
Loughran (10) Patent No.: US 7,377,930 B2
(45) Date of Patent: May 27, 2008

(54) NERVE PROTECTING TUBE

(76) Inventor: Frank Loughran, Route 1, Box 43-S., Kooskia, ID (US) 83539

( * ) Notice: Subject to any disclaimer, the term of this patent is extended or adjusted under 35 U.S.C. 154(b) by 646 days.

(21) Appl. No.: 10/407,774

(22) Filed: Apr. 2, 2003

(65) Prior Publication Data

US 2004/0199187 A1    Oct. 7, 2004

(51) Int. Cl.
*A61B 17/08* (2006.01)
(52) U.S. Cl. .................................................... 606/152
(58) Field of Classification Search ............... 606/152; 623/1.13, 1.44, 1.12; 24/537, 538, 539, 714.6, 24/115 R; 81/176.1, 176.2, 176.3, 176.15; 607/118
See application file for complete search history.

(56) References Cited

U.S. PATENT DOCUMENTS

| | | |
|---|---|---|
| 3,867,728 A | 2/1975 | Stubstad et al. |
| 4,349,921 A | 9/1982 | Kuntz |
| 4,401,112 A | 8/1983 | Rezaian |
| 5,306,308 A | 4/1994 | Gross et al. |
| 5,354,326 A * | 10/1994 | Comben et al. ............. 607/115 |
| 5,545,229 A | 8/1996 | Parsons et al. |
| 5,658,336 A | 8/1997 | Pisharodi |
| 5,865,848 A | 2/1999 | Baker |
| 5,888,220 A | 3/1999 | Felt et al. |
| 5,888,223 A | 3/1999 | Bray, Jr. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,890 A | 4/1999 | Pisharodi |
| 5,919,235 A | 7/1999 | Husson et al. |
| 5,961,554 A | 10/1999 | Janson et al. |
| 5,972,031 A | 10/1999 | Biedermann et al. |
| 5,980,522 A | 11/1999 | Koros et al. |
| 5,989,291 A | 11/1999 | Ralph et al. |
| 6,015,436 A | 1/2000 | Schonhoffer |
| 6,033,438 A | 3/2000 | Bianchi et al. |
| 6,039,761 A | 3/2000 | Li et al. |
| 6,059,829 A | 5/2000 | Schlapfer et al. |
| 6,093,205 A | 7/2000 | McLeod et al. |
| 6,102,949 A | 8/2000 | Biedermann et al. |
| 6,183,517 B1 | 2/2001 | Suddaby |
| 6,193,757 B1 | 2/2001 | Foley et al. |
| 6,200,348 B1 | 3/2001 | Biedermann et al. |
| 6,655,014 B1 * | 12/2003 | Babini ........................ 29/755 |
| 6,980,863 B2 * | 12/2005 | van Venrooij et al. ...... 607/116 |

* cited by examiner

*Primary Examiner*—Julian W Woo
(74) *Attorney, Agent, or Firm*—Robert L. Shaver; Dykas, Shaver & Nipper, LLP (57) ABSTRACT

The device is a tube for placement around a living, human nerve fiber to protect the nerve from external damage. The device includes two concentric tubes, each of which are semi-circular in cross section. The lining tube rotates within the outer tube. Each of the lining tubes has a channel that extends the length of the tube. When the channels of the two tubes are aligned, the spine-protecting device can be slipped over a nerve without injuring the nerve. Once the nerve is safely inside the lining tube, the two tubes can be rotated relative to each other and locked into place, thus forming a protective tube that extends 360 degrees around a section of nerve. This device can be inserted into the opening between the vertebrae through which the nerve extends. Other runs of nerve in the human body can also be protected.

17 Claims, 6 Drawing Sheets

NERVE PROTECTING TUBE

BACKGROUND OF THE INVENTION

1. Field of the Invention

The present invention generally relates to a device and system for use in neurological surgery, and more particularly relates to a tube for protecting a nerve which may be placed on the nerve without disrupting the nerve.

2. Background Information

Back pain is a very common ailment facing people of all ages. It is a major factor contributing to lost workdays, and results in pain, discomfort and immobility to sufferers. Continued suffering often results in surgery.

When an individual suffers from back pain, it is typically caused by compression of a nerve root as it leaves the spinal column. The spinal column consists of vertebrae which are located adjacent to each other, inter-vertebral discs between each of the vertebrae, a spinal column which is inside the vertebrae, and nerve roots which branch off the spinal cord and exit the spinal column through inter-vertebral foramen. The lower back is called the lumbar spine and is made up of five vertebrae and a sacrum. The middle of the back is the thoracic spine and has twelve vertebrae. The neck is the cervical spine and has seven vertebrae. The vertebrae provide both support and protection for the spinal cord. The inter-vertebral discs, which are located between each individual vertebra, connect the vertebrae together and provide cushion and support.

The inter-vertebral disc is a large round ligament which connects the vertebrae together. It is made up of two parts. The outer ring is the annulus, which is the stronger part and is responsible for connecting the vertebrae. The inner area is the nucleus pulpous which is soft and has the consistency of crabmeat. The nucleus pulpous acts as the shock absorber for the spine.

The nerve roots which exit the spinal cord via the inter-vertebral foramen, carry the messages of the central nervous system from the brain to the extremities and back again. The nerve roots can send signals of pain to the brain when they are pinched or irritated by contact with any of the parts of the vertebral column.

When the inter-vertebral discs become herniated or inflamed, they may touch and compress nerve roots passing through the inter-vertebral foramen. When this occurs, the pressure may be felt as pain in the extremities.

In some patients, the components of the spinal column deteriorate so that they no longer perform their supportive and protective function. In these cases, the spinal roots may be compressed and pinched, and some sort of surgery or immobility may be the only treatment. There are a number of prior art devices which are used in such a situation. These include devices which replace a disc, or which hold two discs apart to prevent pinching of the nerve which passes between the vertebrae. Sometimes spacers are inserted into the body of the vertebra to build up a vertebra.

In certain medical conditions, a treatment to various ailments such as epilepsy or chronic pain are treated by applying electricity or an electric field to the region around a nerve. The prior art has insulation of an electrical wire around a nerve. Such an insulation would be an option when treating ailments that are benefited by direct stimulation of nerves by electricity. The nerve protecting tube of the present invention can be used in the same application. It surrounds nerve and is connected by electrical wires to a source of electricity. When indicated by the treatment, electricity is applied to the nerve protecting tube, which has embedded in it a tracing of conductive material that may spiral around the inside, the outside, or both inside and outside of the nerve protecting tube. This strip of conductive material would be of a material that is conductive to electricity but non-corrosive and non-reactive in the human body.

However, none of these options provide a protection for the nerve as it passes leaves the spinal cord and passes through the inter-vertebral foramen or through the carpal tunnel. A protective device for the nerve is difficult to achieve because such a protective device would have to be slipped over the nerve without cutting the nerve, and then closed to protect the nerve from compression. What is needed is a tube which can be placed in an open position for positioning on the nerve, and which can then be moved to a closed position for protecting the nerve. Such a tube would be inserted into the inter-vertebral opening or in other areas in which nerve tissue was to be protected from physical damage and compression. What is also needed is a nerve protecting tube that would allow direct electrical stimulation to a nerve.

Additional objects, advantages and novel features of the invention will be set forth in part in the description which follows and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

The nerve protecting tube of the present invention accomplishes these and other objects. The nerve protecting tube of the present invention is a device which is to be used in neurological surgery, typically to protect a nerve root as it exits the spinal column through the inter-vertebral foramen. The nerve protecting tube of the invention includes a lining tube which is surrounded by an outer tube. The lining tube includes a lining tube wall in which is defined a first channel. The first channel runs the length of the lining tube, and creates an open side through which the nerve can pass. The lining tube also includes one or more gripping means.

The outer tube surrounds the lining tube, and the two tubes may be rotated around each other. The outer tube includes an outer tube wall which defines a second channel, which like the first channel of the lining tube wall, creates an open side for passage of the nerve. When the lining tube and the outer tube are configured so that the first channel and the second channel are congruent, the two tubes may be placed over a nerve. Once in position on the nerve, the two tubes may be rotated in relation to each other to form a 360-degree tube surrounding the nerve. A means is provided to lock the two tubes in a closed position in which the first channel and the second channel are not congruent and thus form a solid tube around the nerve. The lock close means can be achieved in a number of ways. The tubes can be locked closed by friction or by interference fit between the lining and outer tubes. The lock close means can also be formed using a physical device which causes the two tubes to lock in a closed position. This can be in a form of a small depression or detent of which one would be located in the outer tube and one in the lining tube. When the two tubes were in the locked position, these two detents would be in corresponding positions and would interfit to lock the lining and outer tube in a closed position.

The device can further include a means for locking the two tubes in an open position. This can be by a means of friction or interference fit between the two tubes, or can be by the use of the corresponding detents which are described above. The lining tube is provided with one or more gripping means. These gripping means would typically be a socket located on the rim of the lining tube. The socket would be a small depression located on the rim of the lining tube which would be accessible when the tube is in position on the nerve. This socket would be designed for access by the pins of a spanner type wrench, called a tube rotation tool. The outer tube also has a gripping means, which can be by a friction grip such as a pair of pliers would provide by flat sections for a wrench, or by outer tube rim sockets for access by a spanner as described above.

The tube rotation tool can be configured in the form of a device which grips the outer tube by friction and rotates the lining tube by the use of pins which fit in sockets in the rim of the lining tube.

The nerve protecting tube of the invention may also optionally include a keeper, for maintaining the longitudinal alignment of the tubes. This is so that one tube does not slide away from the other tube in a telescoping fashion. The keeper can take a number of forms, such as an interference fit, or a ridge on one tube which interfits with a grove on another tube or a pair of detents which are positioned on either side of the ridge on one tube. The keeper can also be formed by flaring one or both ends of one of the tubes to prevent the tubes from sliding apart.

The device includes a means for holding the tubes in an open position. This is so that they can be stabilized while they are being inserted over the nerve, and do not prematurely close on a nerve. This "lock open means" would typically be corresponding detents in the lining and outer tube. When the two detents were aligned, they would tend to stay together until sufficient rotational force was exerted to move one tube relative to another. An interference fit could also be the lock open means.

The nerve protecting device is designed to be positioned on the segment of human nerve when the lining and outer tubes are in an open position. In the open position, the first and second channels are congruent, or aligned. When the tubes are rotated in relation to each other into a closed position, the nerve is completely enclosed within the two tubes. In the closed position, the two tubes are non-congruent. In the closed position, a lock close means engages and holds the lining tube in a closed position in relation to the outer tube.

The invention also encompasses a nerve protection system, which includes the lining and outer tube described above, and also includes a tool rotation tool, which is configured for gripping the outer tube and the lining gripping means, and rotating the two tubes from a closed into an open position and vise versa. The tube rotation tool can take the form of a pliers like device, which grips the outer tube by a friction fit, and rotates the inner tube by insertion of one or more pins into one or more corresponding sockets on the rim of the lining tube. The tube rotation tool can also take the form of a device which grips both tubes by sockets in each of their respective rims, which provide a grip so that the tubes can be rotated in relation to each other. Flat sections on the outer tube could be provided, to provide gripping means for a wrench.

Further, the purpose of the foregoing abstract is to enable the United States Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measure by the claims, nor is it intended to be limiting as to the scope of the invention in any way.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive.

DESCRIPTION OF THE PREFERRED EMBODIMENTS

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

Although the device can be implemented in a variety of ways within the scope of the claims, one particular preferred embodiment of the invention is described herein. This preferred embodiment is shown in FIGS. 1-5C.

Figure 1:
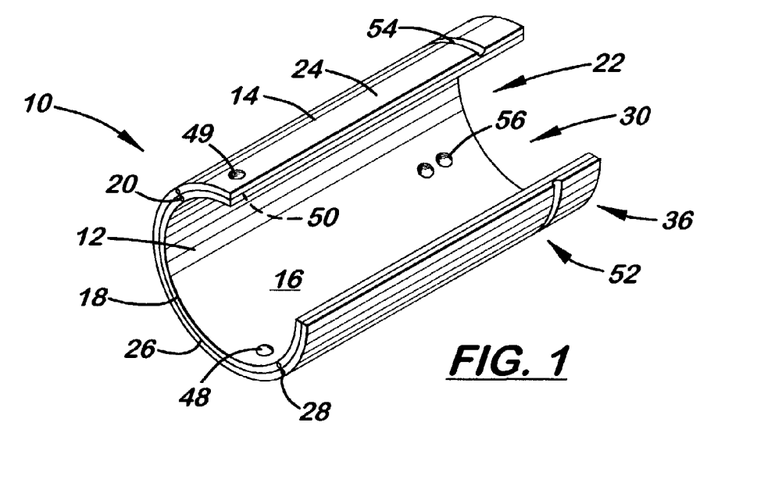
FIG. 1 is a perspective view of the nerve protecting tube of the invention in an open position.

FIG. 1 shows the device in an open position. The device includes a lining tube 12, an outer tube 14, and a lining tube 12, which includes a lining tube wall 16, a lining tube rim 18, and a lining tube rim socket 20. The lining tube wall 16 defines a first channel 22 which runs the length of the lining tube and presents an open side to the nerve. This allows the device to be slipped over the nerve without damaging the nerve. The outer tube 14 includes an outer tube wall 24, an outer tube rim 26, and an outer tube rim socket 28. The outer tube wall 24 defines a second channel 30 which like the first channel runs the length of the outer tube 14, and presents an open side to a nerve. When the first channel 22 and the second channel 30 are congruent, as shown in FIG. 1, the device may be slipped over a nerve.

Figure 2:
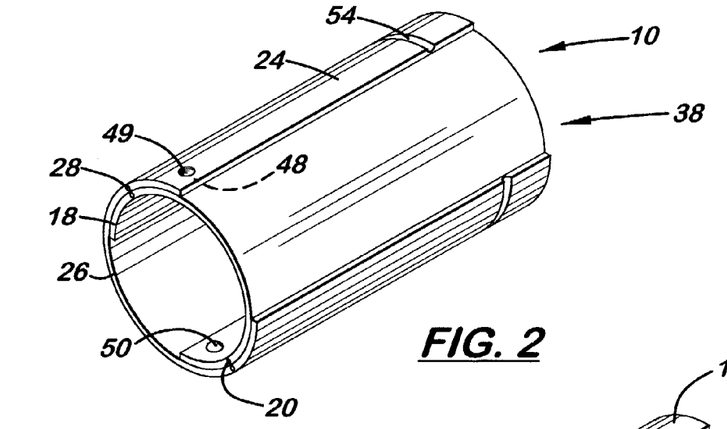
FIG. 2 is a perspective view of the nerve protecting tube in a closed position.

Once over a nerve, the lining tube 12 and the outer tube 14 may be rotated in relation to each other as shown in FIG. 2. This results in a closed position 38 (FIG. 2), as opposed to the open position 36 of FIG. 1.

The device includes a means for locking the tubes in the locked position shown in FIG. 2. This can be by means of friction or interference fit between the tubes, or by various mechanical means. One mechanical means of locking the device closed is by use of a closed position detent 48. When the closed position detent 48 is align with a positioning detent 49 in the opposite tube, the two detents fit together and hold the two tubes in a closed position. Similarly, an open position detent 50 can be used to accomplish holding the two tubes in an open position while they are placed in position.

Optionally, the nerve protecting tube 10 can also include a keeper means 52. The keeper means 52 is to keep the two tubes aligned longitudinally, so that they do not move away from alignment with each other in a telescoping fashion. The keeper means 52 can take a number of forms. An interference fit may serve as the keeper means. The keeper means can be a ridge 54 formed in one of the tubes which is bounded by one or more keeper detents 56, which could be raised features on the corresponding tube which trap the keeper ridge 54 between them. In this way, the two tubes would not telescope out of alignment with each other.

Figure 3:
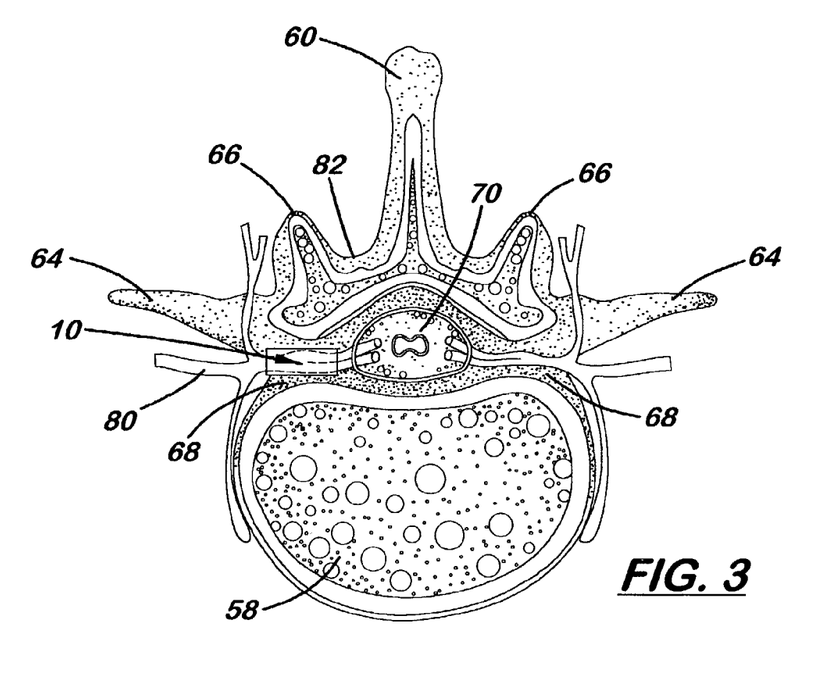
FIG. 3 is a top cross-sectional view of the nerve protecting tube of the invention mounted in the inter-vertebral foramen of a vertebra.

The nerve protecting tube 10 is used to protect a human nerve in any position in which the nerve may be protected. One place where its use is anticipated is in relation to the human spinal column. Details of this type of placement are shown in FIG. 3. The human spinal column includes a spinal process 60, transverse process 64, a vertebra body 58, superior articular process 66, and lamina 82. Between the body 58 of each vertebra is a disc 62. Between the vertebrae is located an inter-vertebral foramen 68 through which a nerve root 80 passes. The nerve root 80 originates in the spinal cord 70 which is located within the vertebra and protected by the bony structure of the vertebral column of the spinal column. As shown in FIG. 3, a preferred use of the nerve protecting tube 10 is to protect the nerve root 80 as it passes through the inter-vertebral foramen 68.

Figure 4:
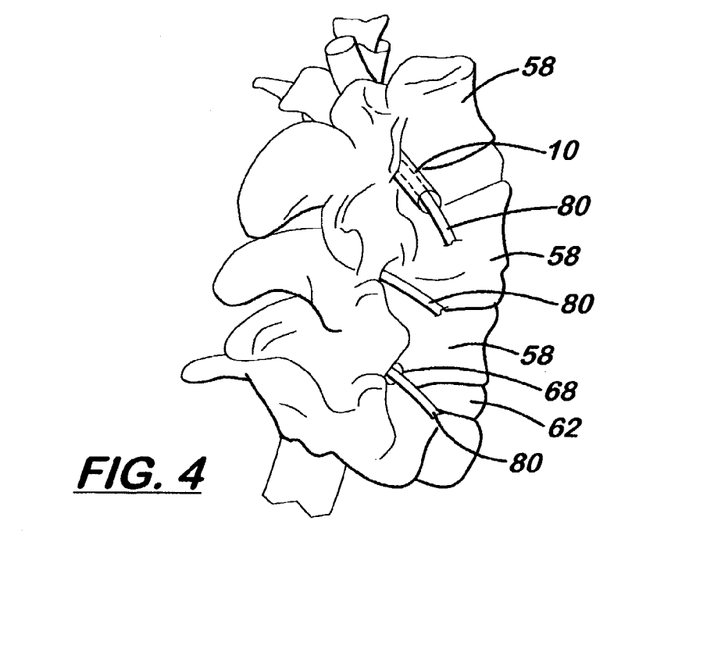
FIG. 4 is a side view of a section of spinal column showing the nerve protecting tube of the invention mounted over a nerve root.

FIG. 4 is a side view of a section of spinal column in which several vertebrae are illustrated with the nerve root 80 extending from the inter-vertebral foramen 68 of each vertebra. In the uppermost illustrated vertebra of FIG. 4, a nerve protecting tube 10 has been installed to protect the nerve root 80.

Figures 5A, 5B:
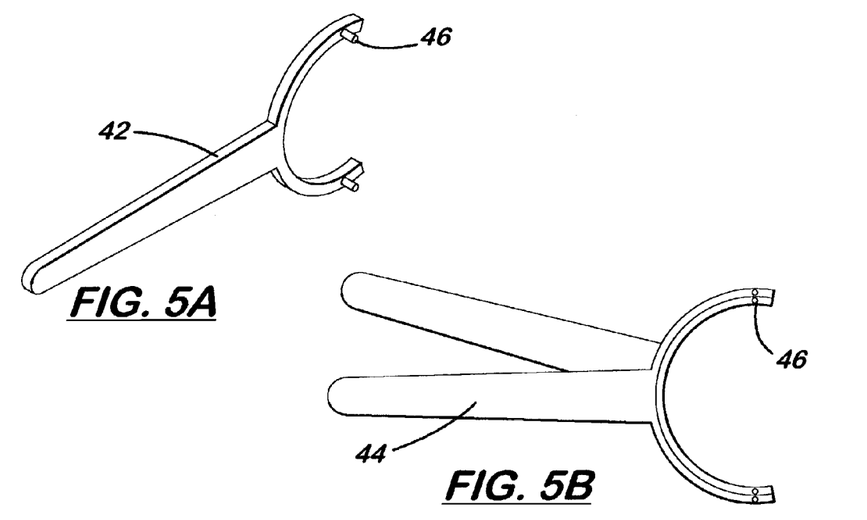
FIG. 5A is a perspective view of a tube rotation tool.
FIG. 5B is an alternative embodiment of a tube rotation tool, in an open position.
Figure 5C:
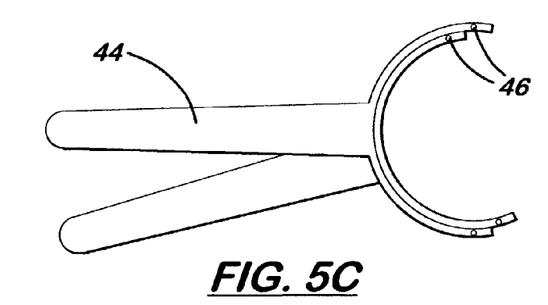
FIG. 5C is the tube rotation tool of FIG. 5B in a closed position.
Figure 6:
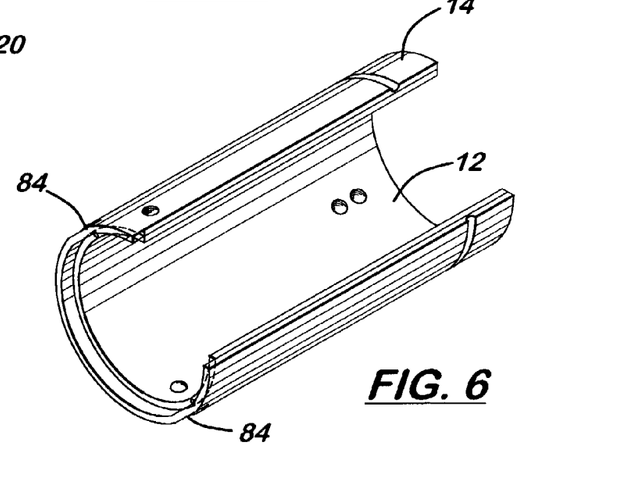
FIG. 6 is the tube with flat sections for gripping by a wrench.

One embodiment of the nerve protecting tube 10 is designed with sockets 28 and 20 in the rim of the outer and lining tubes. The sockets can be accessed with a spanner type wrench as shown in FIG. 5A. FIGS. 5B and 5C show another type wrench which could be utilized to access the rim sockets on both the lining tube and the outer tube, and to turn the two tubes in relation to each other. Another way that the tube can be locked in place is by use of a wrench which grips the outer tube in a pliers like fashion, and which has pins 46 as shown in FIG. 5A. The device shown in FIGS. 5B and 5C is a tube rotation tool 44, which has a number of pins 46 that are configured to operate with the outer tube rim sockets 28 and the lining tube rim sockets 20. A thin open sided wrench could be used to position the outer tube 14, by the use of wrench flats 84, as shown in FIG. 6.

Figure 7:
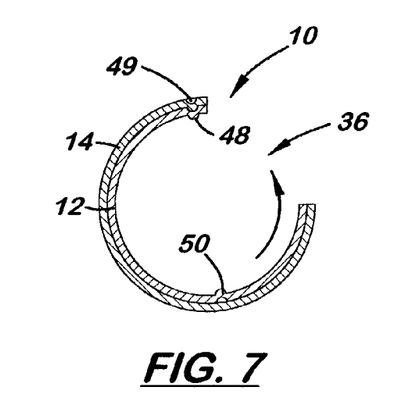
FIG. 7 is a cross-section of the device showing the detents in the open position.
Figure 8:
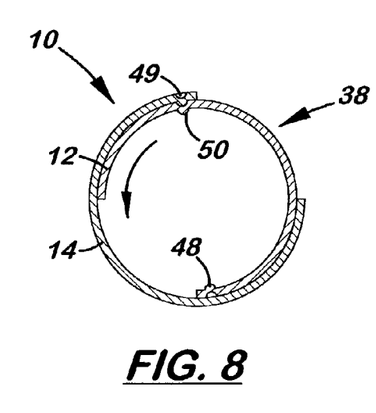
FIG. 8 is a cross-section of the device showing the detents in the closed position.

FIGS. 7 and 8 are cross sections of the device in the open and closed position, showing the interfitting of detents to hold the tubes in an open or closed position.

The nerve protecting tube 10 is made of a material which is suitable for implanting without reaction within the human body. Such materials can include titanium, stainless steel, nylon, Teflon, ceramics, non-corrosive metals, or other materials which are suitable for long-term placement in the body which do not corrode or are not rejected by tissue. The tubes can be lined with a material such as Teflon or nylon which forms a non-irritating surface for nerve tissue.

Figure 9:
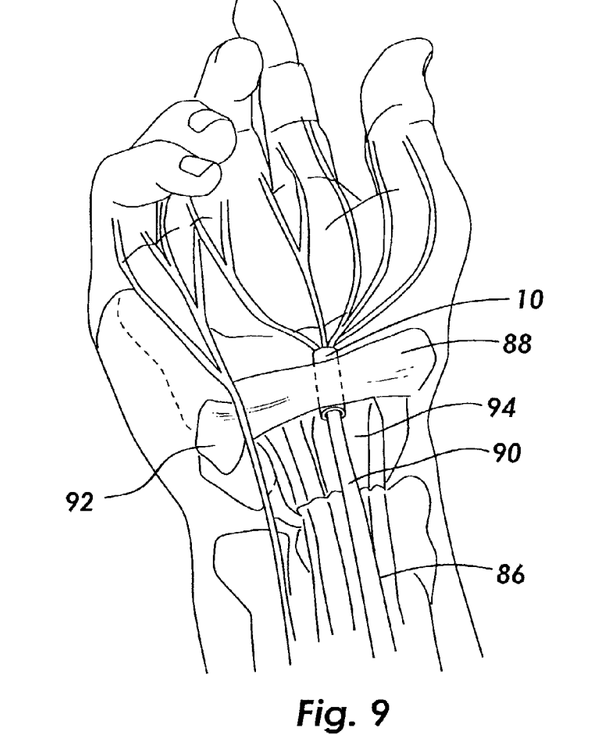
FIG. 9 is a perspective cutaway view of the human hand, showing the nerve protecting tube in position in a carpal tunnel application.

FIG. 9 is a perspective cutaway view of a human wrist showing wrist tendons 86, transverse carpal ligament 88, median nerve 90, carpal bones 92, and tendon sheath 94. These body parts are the location where many patients suffer pain from the wrist nerve being pinched off as it passes through the transverse carpal ligament. FIG. 9 shows a nerve protecting tube 10 of the invention inserted to protect the median nerve 90 from such pressure.

Figure 10:
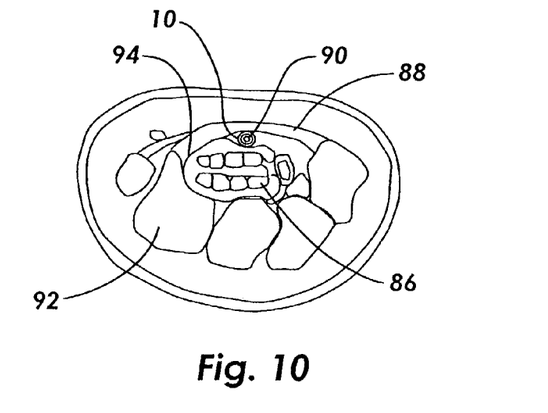
FIG. 10. is a cross section view of the human wrist with the nerve protecting tube in position in a carpal application.

FIG. 10 is a cross-sectional view of the human wrist showing the nerve protecting tube 10 surrounding the median nerve 90, and protecting it from pressure from the structures of the carpal tunnel.

Figure 11:
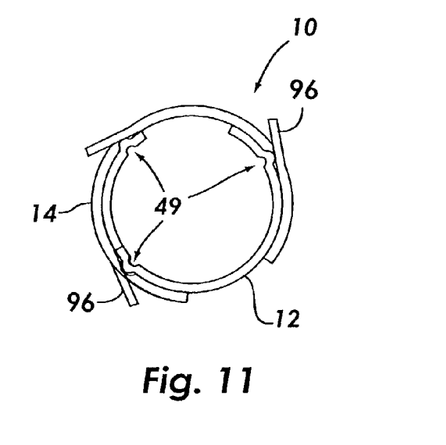
FIG. 11 is a cross section of a version of the nerve protecting tube, showing external positioners.
Figure 12:
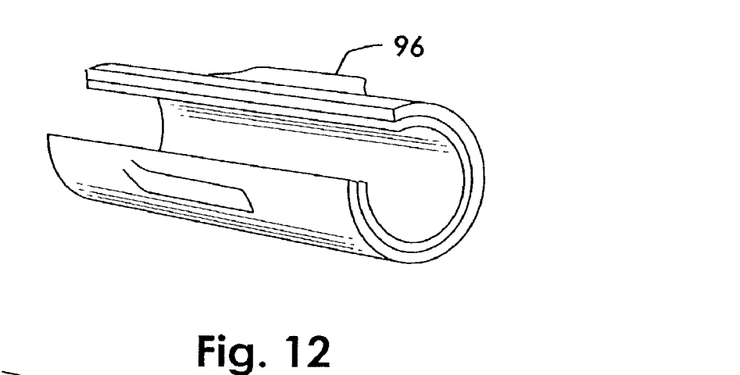
FIG. 12 is a perspective view of the nerve protecting tube, showing external positioners.

FIGS. 11 and 12 show some alternative designs of the nerve protecting tube 10 that include external positioners 96, which protrude from the device and serve to stabilize the device in the human body, and protect it from movement after it is placed.

Figure 13:
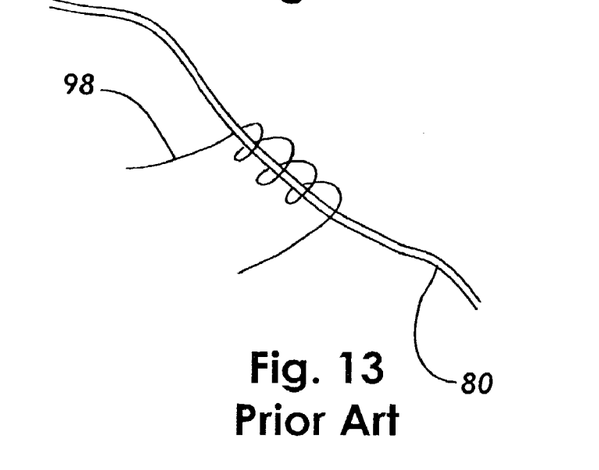
FIG. 13 is a perspective view of prior art method of applying electrical field to nerve.
Figure 14:
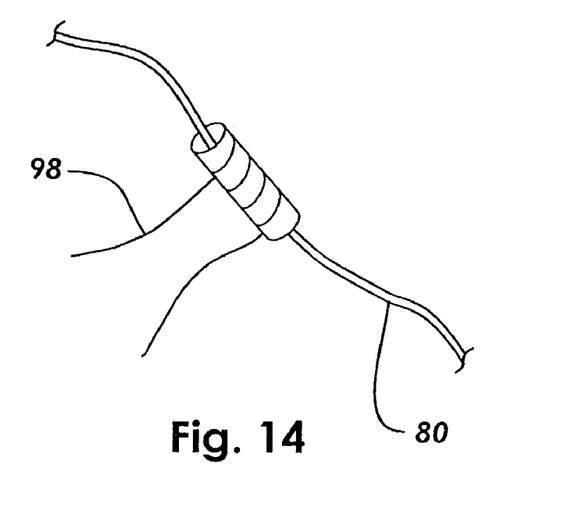
FIG. 14 is perspective view of the nerve protective tube used to apply electrical field to nerve.
Figure 15:
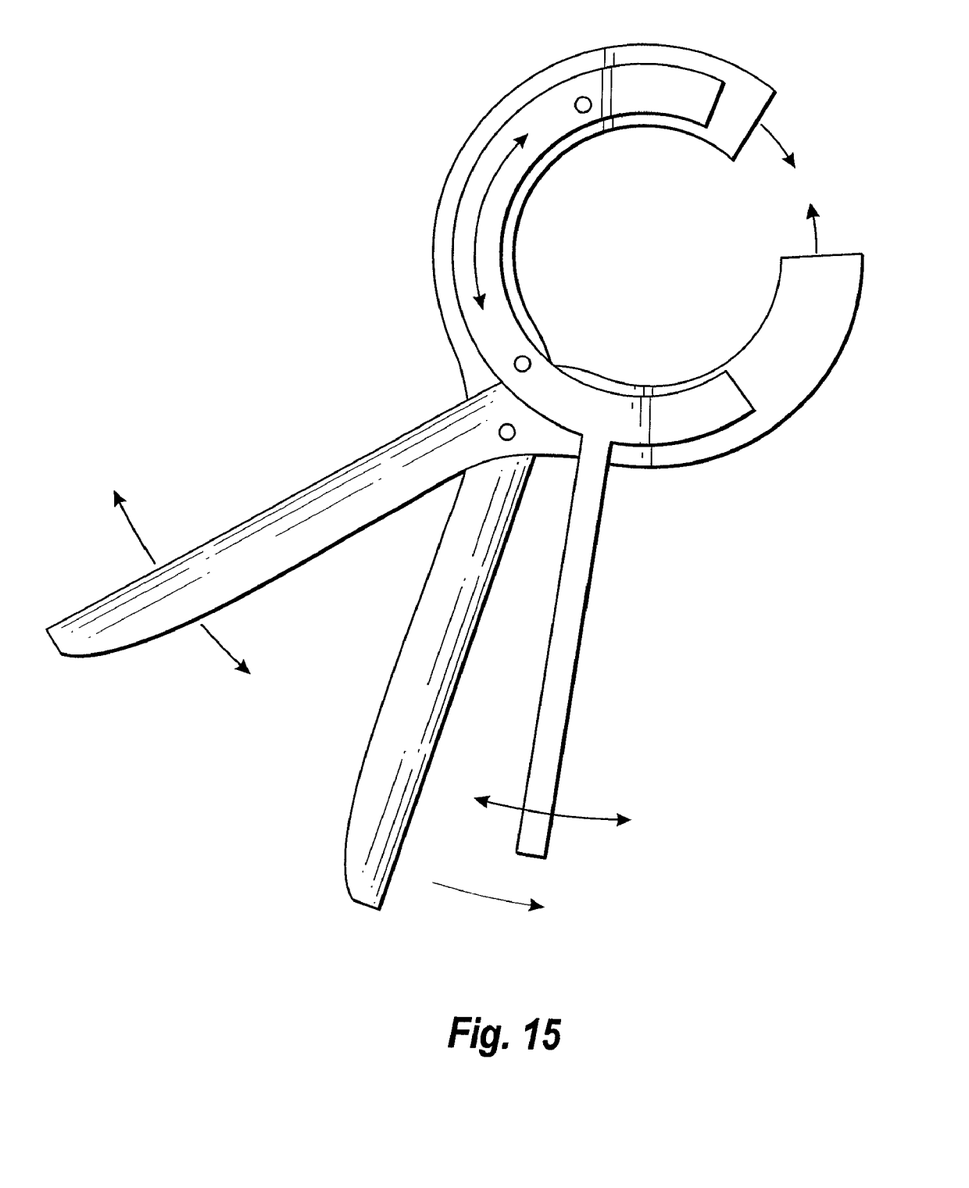
FIG. 15 is a view of a tube gripping tool of the invention.

In certain medical conditions, a treatment to various ailments such as epilepsy or chronic pain are treated by applying electricity or an electric field to the region around a nerve. FIG. 13 shows prior art insulation of an electrical wire 98 around a nerve 80. Such an insulation would be an option when treating ailments that are benefited by direct stimulation of nerves by electricity. FIG. 14 shows the nerve protecting tube of the present invention installed in the same application as FIG. 13. It surrounds nerve 80, and is connected by electrical wires 98 to a source of electricity. When indicated by the treatment, electricity is applied to the nerve protecting tube 10, which has embedded in it a tracing of conductive material that may spiral around the inside, the outside, or both inside and outside of the nerve protecting tube. This strip of conductive material would be of a material that is conductive to electricity but non-corrosive and non-reactive in the human body. This might be gold, silver, or platinum.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

I claim:

1. A nerve protecting tube for use on human nerve fibers, comprising:
   a lining tube with a lining tube wall which defines a first channel which runs the length of said lining tube, and which includes one or more lining tube gripping means said gripping means comprises a socket in the rim of said lining tube, configured for interfitting relationship with a tube rotation tool with a pin, and an outer tube gripper;
   an outer tube which surrounds said lining tube, and which has an outer tube wall which defines a second channel which runs the length of said outer tube, and which is configured for rotation around said lining tube;
   a lock closed means for locking said lining tube and said outer tube in a closed position in which said first channel is not congruent with said second channel;
   wherein said nerve protecting tube is configured for positioning on a segment of human nerve when in an open position with said first and second channels congruent, and for closing on said nerve to a closed position with said lining and outer tubes rotated in relation to each other to make said channels non congruent, in which position said lock closed means engages to hold said lining and said outer tube in said closed position.

2. The nerve protecting tube of claim 1 which further includes a lock open means for locking the tubes in an open position.

3. The nerve protecting tube of claim 2 in which said lock open means is an open position detent in said outer tube and a corresponding open position detent in said lining tube, with said open position detent in said lining tube corresponding in shape to said open position detent in said outer tube, for providing axial and radial limit to movement between the tubes.

4. The nerve protecting tube of claim 1 in which said outer tube gripper is a socket configured for interlocking insertion of a pin.

5. The nerve protecting tube of claim 1 in which said outer tube gripper is a friction gripping device.

6. The nerve protecting tube of claim 1 which includes a pliers device with a pin which interfits with the socket to rotate the lining tube, and in which the outer tube gripper is configured to stabilize the outer tube against rotation in relation to the lining tube.

7. The nerve protecting tube of claim 1 which said lining tube gripping means is one or more lining tube sockets in a rim of said lining tube, configured for interfitting relationship with one or more first positioning pins, and said outer tube includes one or more outer sockets in a rim of said outer tube, configured for interfitting relationship with one or more second positioning pins.

8. The nerve protecting tube of claim 1 in which said lock closed means is a closed position detent in said outer tube and a corresponding closed position detent in said lining tube, with said closed position detent in said lining tube corresponding in shape to said closed position detent in said outer tube, for providing axial and radial limit to movement between the tubes.

9. The nerve protecting tube of claim 1 which further includes a keeper means for maintaining longitudinal alignment of said tubes.

10. The nerve protecting tube of claim 9 in which said keeper means is a ridge on said lining tube, and two keeper detents on said outer tube.

11. A nerve protection system comprising:
    a lining tube with a lining tube wall which defines a first channel which runs the length of said lining tube, and which includes one or more lining tube gripping means;
    an outer tube which surrounds said lining tube, and which has an outer tube wall which defines a second channel which runs the length of said outer tube, and which is configured for rotation around said lining tube;
    a lock closed means for locking said lining tube and said outer tube in a closed position in which said first channel is not congruent with said second channel;
    a tube rotation tool, which is configured for gripping said outer tube and said lining gripping means, and rotating said tubes into a closed position;
    wherein said lining tube and said outer tube are configured for positioning on a segment of nerve when in an open position when said first and second channels are congruent, and said tube rotation tool is configured for closing said tubes on said nerve in a closed position when said lining and said outer tubes are rotated in relation to each other to make said first and second channels non congruent, in which position said lock closed means engages to hold said lining and said outer tube in said closed position.

12. The nerve protection system of claim 11 in which said lock closed means is a closed position detent in said outer tube and a corresponding closed position detent in said lining tube.

13. The nerve protection system of claim 11 which includes a lock open means in the form of an open position detent in said outer tube and a corresponding open position detent in said lining tube.

14. The nerve protection system of claim 11 which further includes a keeper means which maintains longitudinal alignment of said lining tube and said outer tube.

15. The nerve protection system of claim 14 in which said keeper means is a ridge on said lining tube, and two detents on said outer tube.

16. The nerve protecting system of claim 11, in which said rotation tool is configured for gripping said outer tube by friction and gripping said lining tube with a pin inserted into a socket in a rim of said lining tube, and for rotating said lining tube in relation to said outer tube.

17. The nerve protecting system of claim 11, in which said rotation tool is configured for gripping said outer tube with a pin inserted in a rim of said outer tube, and gripping said lining tube with a pin inserted into a socket in a rim of said lining tube, and for rotating said lining tube in relation to said outer tube.

* * * * *